United States Patent
Arhancet

(10) Patent No.: US 6,592,722 B2
(45) Date of Patent: Jul. 15, 2003

(54) POLYMERIZATION INHIBITOR FOR VINYL-CONTAINING MATERIALS

(75) Inventor: Grace B. Arhancet, St. Louis, MO (US)

(73) Assignee: GE Betz, Inc., Trevose, PA (US)

( * ) Notice: Subject to any disclaimer, the term of this patent is extended or adjusted under 35 U.S.C. 154(b) by 0 days.

(21) Appl. No.: 10/235,009

(22) Filed: Sep. 4, 2002

(65) Prior Publication Data

US 2003/0030035 A1 Feb. 13, 2003

Related U.S. Application Data

(62) Division of application No. 09/625,617, filed on Jul. 24, 2000, now Pat. No. 6,447,649.

(51) Int. Cl.$^7$ ............................. B01D 3/34; B01D 3/42
(52) U.S. Cl. .................................................. 203/8; 203/9
(58) Field of Search ........................................ 203/8, 9

*Primary Examiner*—Barbara P. Badio
(74) *Attorney, Agent, or Firm*—Steven D. Boyd

(57) ABSTRACT

This invention relates to a process of inhibiting the polymerization of vinyl-containing materials through the use of an effective amount of a polymerization inhibitor comprising quinone diimide and a nitroxyl stable free radical under various conditions. This invention also relates to the polymerization inhibitor composition.

47 Claims, No Drawings

POLYMERIZATION INHIBITOR FOR VINYL-CONTAINING MATERIALS

This is a divisional of application Ser. No. 09/625,617 filed Jul. 24, 2000, now U.S. Pat. No. 6,447,649.

FIELD OF THE INVENTION

This invention relates to methods and compositions for retarding or inhibiting unwanted polymerization of compounds containing vinyl functionality. More particularly, the present invention relates to methods and compositions for inhibiting the polymerization of vinyl monomers during processing, transportation or storage.

BACKGROUND OF THE INVENTION

Common industrial methods for producing various compounds containing vinyl functionality such as styrene or acrylonitrile typically include separation and purification processes such as distillation to remove unwanted impurities. Unfortunately, purification processes carried out at elevated temperatures result in an increased rate of undesired polymerization. Distillation is generally carried out under vacuum to minimize loss of monomer. The presence of oxygen, although virtually excluded in such processes as styrene distillation, will also promote polymerization of the styrene monomer.

These unwanted polymerizations result not only in loss of desired monomer end products, but also in the loss of production efficiency caused by polymer formation and/or agglomeration of polymer on process equipment.

SUMMARY OF THE INVENTION

The present invention relates to a vinyl functionality polymerization inhibitor comprising a quinone diimide compound and at least one of a stable free radical compound and hydroquinone. The stable free radical compound may comprise a nitroxyl compound. Examples of the stable free radical compound include 2,2,4,4-tetramethyl-4-hydroxy-1-piperidinyloxy (OH-TEMPO) and 2,2,4,4-tetramethyl-4-oxo-1-piperidinyloxy (OXO-TEMPO).

The quinone diimide compound of the present invention comprises a benzoquinonediimide compound. The benzoquinonediimide compound typically has the general formula:

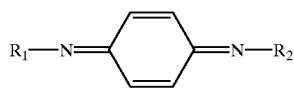

wherein $R_1$ and $R_2$ are the same or different and are alkyl, aryl, alkaryl, or aralkyl groups. Preferably the benzoquinonediimide compound is selected from the group consisting of N,N'-dialkyl-p-benzoquinonediimides and N-phenyl-N'-alkyl-p-benzoquinonediimides. The benzoquinonediimide compound may also be selected from the group consisting of N,N'-di-sec-butyl-p-benzoquinonediimide, N-phenyl-N'-methyl-p-benzoquinonediimide, N-phenyl-N'-ethyl-p-benzoquinonediimide, N-phenyl-N'propyl-p-benzoquinonediimide, N-phenyl-N'-n-butyl-p-benzoquinonediimide, N-phenyl-N'-isobutyl-p-benzoquinonediimide, N-phenyl-N'-sec-butyl-p-benzoquinonediimide, N-phenyl-N'-tert-butyl-p-benzoquinonediimide, N-phenyl-N'-n-pentyl-p-benzoquinonediimide, N-phenyl-N'-(1-methylhexyl)-p-benzoquinonediimide, and N-phenyl-N'-(1,3-dimethylhexyl)-p-benzoquinonediimide.

A preferred benzoquinonediimide compound comprises N-{4-[(1,3-dimethylbutyl)imino]-2,5-cyclohexadien-1-ylidine}, also named [4-(1,3-dimethyl-butylimino)-cyclohexa-2,5-dienylidene]-phenyl-amine, and which is available from Flexsys under the product names Q-Flex QDI and 6-QDI.

In the vinyl functionality polymerization inhibitor of the present invention the ratio of quinone diimide to the at least one of the stable free radical compound and hydroquinone can range by weight in a ratio of from about 1:20 to about 20:1, preferably of from about 1:10 to about 10:1, more preferably of from about 1:3 to about 3:1, more preferably of from about 1:1.

The present invention also relates to a method for inhibiting the polymerization of compositions comprising vinyl functionality comprising adding to the compositions comprising vinyl functionality an effective amount of the vinyl functionality polymerization inhibitor. The compositions comprising vinyl functionality may be selected from the group consisting of vinyl chloride, vinyl acetate, methylmethacrylate, acrylonitrile, methacrylonitrile, acrylic acid, methacrylic acid, styrene, α-methylstyrene and vinyltoluene.

The present invention also relates to compositions comprising the compositions comprising vinyl functionality and the vinyl functionality polymerization inhibitor.

DETAILED DESCRIPTION OF THE INVENTION

The present invention relates to a method for inhibiting the undesired polymerization of compositions comprising vinyl functionality. The compositions comprising vinyl functionality are characterized by having a $CH_2=CH-$ group and are highly reactive and polymerize easily. Examples of such compositions comprising vinyl functionality include vinyl monomers such as vinyl chloride, vinyl acetate and similar unsaturated esters, methylmethacrylate, acrylonitrile, methacrylonitrile, acrylic acid, methacrylic acid and their esters and amides, styrene, α-methylstyrene, vinyltoluene. Preferably, the compositions comprising vinyl functionality comprises vinyl monomers selected from the group consisting of vinyl chloride, vinyl acetate, methylmethacrylate, acrylonitrile, methacrylonitrile, acrylic acid, methacrylic acid, styrene, α-methylstyrene and vinyltoluene.

Preferably the invention relates to a process for inhibiting the polymerization of monomers comprising vinyl functionality, such as acrylonitrile or styrene. The compositions may be a composition which contains vinyl functionality such as an oligomer or, more preferably, the composition which contains vinyl functionality is a vinyl monomer.

For the purposes of this invention, the term "effective amount" refers to the amount of a vinyl polymerization inhibitor necessary to retard or inhibit the polymerization of the composition which contains vinyl functionality as determined by an increase in the length of the induction period for the presence of polymer under a set of conditions which would typically be conducive of polymerization. This amount will vary according to the conditions under which the composition that contains vinyl functionality is subject during its processing, handling and/or storage The quinone diimide of use in vinyl polymerization inhibitors of the present invention may be any quinone diimide. Preferably, the quinone diimide of the present invention is a benzoquinonediimide compound. The benzoquinonediimide compound of use in the present invention is described in U.S. Pat. No. 5,562,863, the disclosure of which is incorporated in its entirety by reference. The benzoquinonediimide has the general formula:

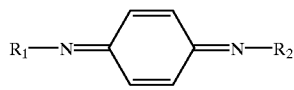

wherein $R_1$ and $R_2$ are the same or different and are alkyl, aryl, alkaryl, or aralkyl groups. Preferably, these groups have one to about 20 carbon atoms and the alkyl groups can be straight-chained, branch-chained, or cyclic groups.

The benzoquinonediimide compound may be selected from the group consisting of N,N'-dialkyl-p-benzoquinonediimides and N-phenyl-N'-alkyl-p-benzoquinonediimides. The benzoquinonediimide compound may also be selected from the group consisting of N,N'-di-sec-butyl-p-benzoquinonediimide, N-phenyl-N'-methyl-p-benzoquinonediimide, N-phenyl-N'-ethyl-p-benzoquinonediimide, N-phenyl-N'propyl-p-benzoquinonediimide, N-phenyl-N'-n-butyl-p-benzoquinonediimide, N-phenyl-N'-isobutyl-p-benzoquinonediimide, N-phenyl-N'-sec-butyl-p-benzoquinonediimide, N-phenyl-N'-tert-butyl-p-benzoquinonediimide, N-phenyl-N'-n-pentyl-p-benzoquinonediimide, N-phenyl-N'-(1-methylhexyl)-p-benzoquinonediimide, and N-phenyl-N'-(1,3-dimethylhexyl)-p-benzoquinonediimide.

A preferred benzoquinonediimide compound comprises N{4-[(1,3-dimethylbutyl)imino]-2,5-cyclohexadien-1-ylidine}, also named [4-(1,3-dimethyl-butylimino)-cyclohexa-2,5-dienylidene]-phenyl-amine, and which is available from Flexsys under the product names Q-Flex QDI and 6-QDI.

In addition to the quinone diimide, the vinyl functionality polymerization inhibitor also comprises an amount of at least one of a stable free radical compound, such as nitroxyls, or hydroquinone. It has been determined that the use of the at least one of the stable free radical compound or hydroquinone has a synergistic effect on the vinyl polymerization inhibition of quinone diimide.

The stable free radical compound comprises nitroxyl compounds. Among the nitroxyl compounds of use with the quinone diimide are selected from the group consisting of 2,2,4,4-tetramethyl-4-hydroxy-1-piperidinyloxy (OH-TEMPO) and 2,2,4,4-tetramethyl-4-oxo-1-piperidinyloxy (OXO-TEMPO).

The ratio of quinone diimide to the at least one of the stable free radical compound or hydroquinone can range by weight in a ratio of from about 1:20 to about 20:1, preferably, in a ratio of from about 1:10 to about 10:1, more preferably in a ratio of from about 1:3 to about 3:1, more preferably about 1:1.

Preferably, an effective amount of the vinyl functionality polymerization inhibitor comprising quinone diimide and at least one of the stable free radical compound and/or hydroquinone is added to the composition containing vinyl functionality to retard or inhibit unwanted polymerization of the vinyl groups contained in the composition containing vinyl functionality. The vinyl functionality polymerization inhibitor may be added to the composition containing vinyl functionality in a range by weight of from about 0.5 parts vinyl polymerization inhibitor to about 10,000 parts per million to the composition which contains vinyl functionality. More preferably, the amount of vinyl polymerization inhibitor added to the composition which contains vinyl functionality ranged from about 1 part to about 500 parts per million of the composition which contains vinyl functionality.

The vinyl functionality polymerization inhibitor may be added to the compounds containing vinyl functionality directly, as dispersion or as a solution using a suitable liquid carrier or solvent. Any liquid carrier or solvent that is compatible with the composition containing vinyl functionality and the vinyl functionality polymerization inhibitor.

The compositions of the present invention prove effective in inhibiting polymerization of compounds containing vinyl functionality as these compounds are subjected to such typical processing steps as distillation and purification.

The following examples are meant for illustrative purposes only and are not to be construed as limiting the present invention in any manner whatsoever.

EXAMPLES

All amounts listed in the following examples are by weight, unless otherwise specified.

Example 1

Uninhibited acrylonitrile (10 ml) was placed in a 50 ml pressure glass tubes fitted with stoppers. The various dosages of the vinyl polymerization inhibitor were added to the uninhibited acrylonitrile and the glass tubes were closed and immersed in and oil bath heated at 110° C. Every 30 minutes, the tubes were inspected for turbidity for the presence of polymer. The time when the presence of polymer was observed was noted.

OH-TEMPO: 2,2,4,4-tetramethyl-4-hydroxy-1-piperidinyloxy

BQDI: Benzamine, N-{4-[(1,3-dimethylbutyl)imino]-2,5-cyclohexadien-1-ylidine}

The results are found in Tables 1 and 2 hereinbelow.

TABLE 1

| INHIBITOR | DOSE (ppm) | INDUCTION TIME (h) |
|---|---|---|
| Blank (comparative) | — | 1 |
| HQ (comparative) | 10 | 12 |
| OH-TEMPO (comparative) | 5 | 60 |
| BQDI (comparative) | 5 | 136 |
| OH-TEMPO/BQDI | 5/5 | 302 |
| OH-TEMPO (comparative) | 10 | 120 |
| BQDI (comparative) | 10 | 188 |

TABLE 2

| INHIBITOR | DOSE (ppm) | INDUCTION TIME (h) |
|---|---|---|
| Blank (comparative) | — | 1 |
| HQ (comparative) | 10 | 12 |
| BQDI (comparative) | 5 | 136 |
| BQDI (comparative) | 10 | 188 |
| BQDI/HQ | 5/5 | 500 |
| BQDI/HQ | 10/10 | 840 |

The results as found in Tables 1 and 2 indicate that benzoquinonediimide (BQDI) was found to have a synergistic effect with stable free radicals and with hydroquinone (HQ) respectively in inhibiting the thermal polymerization of acrylonitrile.

Example 2

Uninhibited styrene (5 ml) was placed in test tubes and various amounts of the vinyl polymerization inhibitor were added to the various test tubes. The tubes were capped with rubber septums and argon gas was bubbled through the contents of the test tubes at a rate of 10 ml/min for a period of 3 minutes. The tubes were then placed in an oil bath heated to a temperature of 110° C. for a period of two hours.

OXO-TEMPO: 2,2,4,4-tetramethyl-4-oxo-1-piperidinyloxy.

The amount of polystyrene formed in the test tube was determined using methanol precipitation.

The results of this experiment are found in Table 3.

TABLE 3

| INHIBITOR | DOSE (ppm) | % POLYMER |
| --- | --- | --- |
| Blank (comparative) | — | 7.05 |
| OH-TEMPO (comparative) | 100 | 1.47 |
| OH-TEMPO (comparative) | 200 | 0.04 |
| BQDI (comparative) | 300 | 4.82 |
| BQDI/OH-TEMPO | 100/100 | 0.05 |
| " | 67/133 | 0.03 |
| " | 133/67 | 0.97 |
| OXO-TEMPO (comparative) | 100 | 1.99 |
| OXO-TEMPO (comparative) | 200 | 0.52 |
| BQDI/OXO-TEMPO | 100/100 | 0.43 |
| " | 200/100 | 0.06 |
| " | 200/200 | 0.00 |

The results as found in Table 3 indicate that OXO-TEMPO: 2,2,4,4-tetramethyl-4-oxo-1-piperidinyloxy and benzoquinonediimide (BQDI) and OH-TEMPO: 2,2,4,4-tetramethyl-4-hydroxy-1-piperidinyloxy were found to be effective in inhibiting the thermal polymerization of styrene and that the combination of BQDI and OXO-TEMPO was found to have a synergistic effect in the inhibition of thermal polymerization of styrene.

It is not intended that the examples given here should be construed to limit the invention, but rather, they are submitted to illustrate some of the specific embodiments of the invention. Various modifications and variations of the present invention known to those of ordinary skill in the art can be made without departing from the scope of the invention.

I claim:

1. A vinyl functionality polymerization inhibitor comprising a quinone diimide compound and a nitroxyl compound.

2. The vinyl functionality polymerization inhibitor of claim 1 wherein the nitroxyl compound comprises 2,2,4,4-tetramethyl-4-hydroxy-1-piperidinyloxy (OH-TEMPO).

3. The vinyl functionality polymerization inhibitor of claim 1 wherein the nitroxyl compound comprises 2,2,4,4-tetramethyl-4-oxo-1-piperidinyloxy (OXO-TEMPO).

4. The vinyl functionality polymerization inhibitor of claim 1 wherein the quinone diimide compound comprises a benzoquinonediimide compound.

5. The vinyl functionality polymerization inhibitor of claim 4 wherein the benzoquinonediimide compound has the general formula:

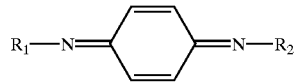

wherein $R_1$ and $R_2$ are the same or different and are alkyl, aryl, alkaryl, or aralkyl groups.

6. The vinyl functionality polymerization inhibitor of claim 5 wherein the benzoquinonediimide compound is selected from the group consisting of N,N'-dialkyl-p-benzoquinonediimides and N-phenyl-N'-alkyl-p-benzoquinonediimides.

7. The vinyl functionality polymerization inhibitor of claim 5 wherein the benzoquinonediimide compound is selected from the group consisting of N,N'-di-sec-butyl-p-benzoquinonediimide, N-phenyl-N'-methyl-p-benzoquinonediimide, N-phenyl-N'-ethyl-p-benzoquinonediimide, N-phenyl-N'propyl-p-benzoquinonediimide, N-phenyl-N'-n-butyl-p-benzoquinonediimide, N-phenyl-N'-isobutyl-p-benzoquinonediimide, N-phenyl-N'-sec-butyl-p-benzoquinonediimide, N-phenyl-N'-tert-butyl-p-benzoquinonediimide, N-phenyl-N'-n-pentyl-p-benzoquinonediimide, N-phenyl-N'-(1-methylhexyl)-p-benzoquinonediimide, and N-phenyl-N'-(1,3-dimethylhexyl)-p-benzoquinonediimide.

8. The vinyl functionality polymerization inhibitor of claim 5 wherein the benzoquinonediimide compound comprises N-{4-[(1,3-dimethylbutyl)imino]-2,5-cyclohexadien-1-ylidine}.

9. The vinyl functionality polymerization inhibitor of claim 1 wherein the ratio of quinone diimide to nitroxyl compound can range by weight in a ratio of from about 1:20 to about 20:1.

10. The vinyl functionality polymerization inhibitor of claim 9 wherein the ratio of quinone diimide to nitroxyl compound can range by weight in a ratio of from about 1:10 to about 10:1.

11. The vinyl functionality polymerization inhibitor of claim 10 wherein the ratio of quinone diimide to nitroxyl compound can range by weight in a ratio of from about 1:3 to about 3:1.

12. The vinyl functionality polymerization inhibitor of claim 11 wherein the ratio of quinone diimide to nitroxyl compound can range by weight in a ratio of from about 1:1.

13. A method for inhibiting the polymerization of compositions comprising vinyl functionality comprising adding to the compositions comprising vinyl functionality an effective amount of vinyl functionality polymerization inhibitor comprising a quinone diimide compound and a nitroxyl compound.

14. The method of claim 12 wherein the quinone diimide compound comprises a benzoquinonediimide compound.

15. The method of claim 14 wherein the benzoquinonediimide compound has the general formula:

wherein $R_1$ and $R_2$ are the same or different and are alkyl, aryl, alkaryl, or aralkyl groups.

16. The method of claim 15 wherein the benzoquinonediimide compound is selected from the group consisting of N,N'-di-sec-butyl-p-benzoquinonediimide, N-phenyl-N'-methyl-p-benzoquinonediimide, N-phenyl-N'-ethyl-p- benzoquinonediimide, N-phenyl-N'propyl-p-benzoquinonediimide, N-phenyl-N'-n-butyl-p-benzoquinonediimide, N-phenyl-N'-isobutyl-p-benzoquinonediimide, N-phenyl-N'-sec-butyl-p-benzoquinonediimide, N-phenyl-N'-tert-butyl-p-benzoquinonediimide, N-phenyl-N'-n-pentyl-p-benzoquinonediimide, N-phenyl-N'-(1-methylhexyl)-p-benzoquinonediimide, and N-phenyl-N'-(1,3-dimethylhexyl)-p-benzoquinonediimide.

17. The method of claim 15 wherein the benzoquinonediimide compound comprises N-{4-[(1,3-dimethylbutyl)imino]-2,5-cyclohexadien-1-ylidine}.

18. The method of claim 13 wherein the ratio of quinone diimide to nitroxyl compound can range by weight in a ratio of from about 1:20 to about 20:1.

19. The method of claim 18 wherein the ratio of quinone diimide to nitroxyl compound can range by weight in a ratio of from about 1:10 to about 10:1.

20. The method of claim 19 wherein the ratio of quinone diimide to nitroxyl compound can range by weight in a ratio of from about 1:3 to about 3:1.

21. The method of claim 20 wherein the ratio of quinone diimide to nitroxyl compound can range by weight in a ratio of from about 1:1.

22. The method of claim 13 wherein the vinyl polymerization inhibitor is added to the composition containing vinyl functionality in a range by weight of from about 0.5 parts vinyl polymerization inhibitor to about 10,000 parts per million to the composition which contains vinyl functionality.

23. The method of claim 22 wherein the vinyl polymerization inhibitor is added to the composition containing vinyl functionality in a range by weight of from about 1 part vinyl polymerization inhibitor to about 500 parts per million of the composition which contains vinyl functionality.

24. The method of claim 13 wherein the vinyl polymerization inhibitor is added to the composition containing vinyl functionality as a dispersion.

25. The method of claim 13 wherein the vinyl polymerization inhibitor is added to the composition containing vinyl functionality as a solution.

26. The method of claim 13 wherein the nitroxyl compound comprises 2,2,4,4-tetramethyl-4-hydroxy-1-piperidinyloxy (OH-TEMPO).

27. The method of claim 13 wherein the nitroxyl compound comprises 2,2,4,4-tetramethyl-4-oxo-1-piperidinyloxy (OXO-TEMPO).

28. The method of claim 13 wherein the vinyl functional polymerization inhibitor comprises benzoquinonediimide and 2,2,4,4-tetramethyl-4-hydroxyl-1-piperidinyloxy (OH-TEMPO).

29. The method of claim 13 wherein the vinyl functional polymerization inhibitor comprises benzoquinonediimide and 2,2,4,4-tetramethyl-4-oxo-1-piperidinyloxy (OXO-TEMPO).

30. A composition comprising a composition comprising vinyl functionality and an effective amount of vinyl functionality polymerization inhibitor comprising a quinone diimide compound and a nitroxyl compound.

31. The composition of claim 30 wherein the composition comprising vinyl functionality comprises vinyl monomers selected from the group consisting of vinyl chloride, vinyl acetate, methylmethacrylate, acrylonitrile, methacrylonitrile, acrylic acid, methacrylic acid, styrene, α-methylstyrene and vinyltoluene.

32. The composition of claim 30 wherein the quinone diimide compound comprises a benzoquinonediimide compound.

33. The composition of claim 32 wherein the benzoquinonediimide compound has the general formula:

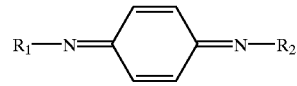

wherein $R_1$ and $R_2$ are the same or different and are alkyl, aryl, alkaryl, or aralkyl groups.

34. The composition of claim 33 wherein the benzoquinonediimide compound is selected from the group consisting of N,N'-di-sec-butyl-p-benzoquinonediimide, N-phenyl-N'-methyl-p-benzoquinonediimide, N-phenyl-N'-ethyl-p-benzoquinonediimide, N-phenyl-N'propyl-p-benzoquinonediimide, N-phenyl-N'-n-butyl-p-benzoquinonediimide, N-phenyl-N'-isobutyl-p-benzoquinonediimide, N-phenyl-N'-sec-butyl-p-benzoquinonediimide, N-phenyl-N'-tert-butyl-p-benzoquinonediimide, N-phenyl-N'-n-pentyl-p-benzoquinonediimide, N-phenyl-N'-(1-methylhexyl)-p-benzoquinonediimide, and N-phenyl-N'-(1,3-dimethylhexyl)-p-benzoquinonediimide.

35. The composition of claim 33 wherein the benzoquinonediimide compound comprises N-{4-[(1,3-dimethylbutyl)imino]-2,5-cyclohexadien-1-ylidine}.

36. The composition of claim 30 wherein the ratio of quinone diimide to nitroxyl compound can range by weight in a ratio of from about 1:20 to about 20:1.

37. The composition of claim 36 wherein the ratio of quinone diimide to nitroxyl compound can range by weight in a ratio of from about 1:10 to about 10:1.

38. The composition of claim 37 wherein the ratio of quinone diimide to nitroxyl compound can range by weight in a ratio of from about 1:3 to about 3:1.

39. The composition of claim 38 wherein the ratio of quinone diimide to nitroxyl compound can range by weight in a ratio of from about 1:1.

40. The composition of claim 30 wherein the vinyl polymerization inhibitor is in a range by weight of from about 0.5 parts vinyl polymerization inhibitor to about 10,000 parts per million to the composition which contains vinyl functionality.

41. The composition of claim 40 wherein the vinyl polymerization inhibitor is in a range by weight of from about 1 part vinyl polymerization inhibitor to about 500 parts per million of the composition which contains vinyl functionality.

42. The composition of claim 30 wherein the vinyl polymerization inhibitor is a dispersion.

43. The composition of claim 30 wherein the vinyl polymerization inhibitor is a solution.

44. The composition of claim 30 wherein the nitroxyl compound comprises 2,2,4,4-tetramethyl-4-hydroxy-1-piperidinyloxy (OH-TEMPO).

45. The composition of claim 30 wherein the nitroxyl compound comprises 2,2,4,4-tetramethyl-4-oxo-1-piperidinyloxy (OXO-TEMPO).

46. The composition of claim 30 wherein the vinyl functional polymerization inhibitor comprises benzoquinonediimide and 2,2,4,4-tetramethyl-4-hydroxy-1-piperidinyloxy (OH-TEMPO).

47. The composition of claim 30 wherein the vinyl functional polymerization inhibitor comprises benzoquinonediimide and 2,2,4,4-tetramethyl-4-oxo-1-piperidinyloxy (OXO-TEMPO).

* * * * *